United States Patent
Becker et al.

(10) Patent No.: US 6,452,384 B1
(45) Date of Patent: Sep. 17, 2002

(54) SCANNING HEAD FOR EDDY-CURRENT TESTING, METHOD FOR PROCESSING A SCANNING HEAD FOR AN EDDY-CURRENT TEST METHOD

(75) Inventors: Erich Becker, Marl; Hans-Peter Lohmann, Wesel-Obrighoven; Gabriel Daalmans, Höchstadt; Klaus Ludwig, Weissenburg; Ludwig Bär, Erlangen, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/564,670

(22) Filed: May 4, 2000

Related U.S. Application Data

(63) Continuation of application No. PCT/DE98/03108, filed on Oct. 22, 1998.

(30) Foreign Application Priority Data

Nov. 4, 1997  (DE) .......................................... 197 48 551

(51) Int. Cl.⁷ .......................... G01N 27/90; G01R 33/02
(52) U.S. Cl. ...................... 324/240; 324/219; 324/228; 324/248
(58) Field of Search ................................ 324/240, 228, 324/232, 233, 234, 236, 237, 239, 241, 242, 243, 248

(56) References Cited

U.S. PATENT DOCUMENTS

| | | | | |
|---|---|---|---|---|
| 4,547,962 A | | 10/1985 | de Walle et al. ............... 29/606 |
| 4,593,245 A | * | 6/1986 | Viertl et al. .................. 324/238 |
| 4,719,422 A | * | 1/1988 | deWalle et al. .............. 324/248 |
| 5,047,719 A | | 9/1991 | Johnson ....................... 324/242 |
| 5,150,042 A | * | 9/1992 | Look et al. .............. 324/158 R |
| 5,262,722 A | * | 11/1993 | Hedengren et al. .......... 342/242 |
| 5,289,121 A | * | 2/1994 | Kajola et al. ................ 324/248 |
| 5,315,234 A | * | 5/1994 | Sutton, Jr. et al. ........... 324/242 |
| 5,371,461 A | | 12/1994 | Hedengren .................... 324/225 |
| 5,389,876 A | * | 2/1995 | Hedengren et al. .......... 324/242 |
| 5,610,517 A | * | 3/1997 | Ma et al. ...................... 324/233 |
| 5,841,277 A | * | 11/1998 | Hedengren et al. .......... 324/240 |
| 5,903,147 A | * | 5/1999 | Granger, Jr. et al. ........ 324/219 |

FOREIGN PATENT DOCUMENTS

| | | | |
|---|---|---|---|
| DE | 3532520 A1 | * 3/1987 | ............ A61B/5/08 |
| DE | 30 50 497 C2 | 8/1988 | |
| EP | 0 228 177 A2 | 7/1987 | |
| EP | 0 512 796 A2 | 11/1992 | |

OTHER PUBLICATIONS

"Zerstörungsfreie Werkstück—und Werkstoffprüfung" (Steeb et al.), dated 1993, Expert Verlag, pp. 490–554, pertains to the non–destructive workpiece and material testing, as mentioned on p. 2 of the specification.

"Hochtemperatur–SQIDs als Wirbelstromdetektoren" (Maass et al.), dated 1996, Carl Hanser Verlag, pp. 431–434, pertains to a high temperatur SQIDs as Eddy–current detectors.

"Zerstörungsfreie Messung der Korrosionseinwirkung auf Hochtemperaturschutz–schichten" (Dibelius et al.), undated 1990, VGB Kraftwerkstechnik 70, pp. 762–768.

\* cited by examiner

*Primary Examiner*—Edward Lefkowitz
*Assistant Examiner*—Darrell D. Kinder
(74) *Attorney, Agent, or Firm*—Laurence A. Greenberg; Werner H. Stemer; Ralph E. Locher

(57) ABSTRACT

A scanning head for eddy-current testing includes a probe coil configuration disposed on a film on a film base. The film base is matched to a shape of an object to be tested. This allows quick, low-interference eddy-current testing. A method for producing a scanning head for an eddy-current test and an eddy-current test method are also provided.

15 Claims, 5 Drawing Sheets

SCANNING HEAD FOR EDDY-CURRENT TESTING, METHOD FOR PROCESSING A SCANNING HEAD FOR AN EDDY-CURRENT TEST METHOD

CROSS-REFERENCE TO RELATED APPLICATION

This application is a continuation of copending International Application No. PCT/DE98/03108, filed Oct. 22, 1998, which designated the United States.

BACKGROUND OF THE INVENTION

FILED OF THE INVENTION

The invention relates to a scanning head for eddy-current testing and to a method for producing such a scanning head. The invention furthermore relates to an eddy-current test method.

An article entitled "Non-destructive Testing of Corrosion Effect on High-temperature Protective Coatings" by G. Dibelius, H. J. Krichel and U. Reimann, in VGB Kraftwerkstechnik 70 (1990), No. 9 describes an eddy-current test on gas turbine blades. Gas-turbine blades are subject to severe mechanical and thermal stresses. Testing such blades for material faults, such as cracks, is essential to operational safety. Gas-turbine blades are, as a rule, provided with a protective coating. The quality of that coating can be checked, inter alia, by using an eddy-current test method. In that case, an excitation coil is used to produce a magnetic alternating field which causes eddy currents in the material to be tested. The eddy currents in turn cause a magnetic alternating field, which is measured by using a detector coil. Material faults have a characteristic influence on the measured magnetic field, and can thus be detected.

A book entitled "Zerstörungsfreie Werkstück- und Werkstoffprüfung" [Non-destructive Workpiece and Material Testing] by Siegfried Steeb, Expert-Verlag Böblingen, 1988, mentions that one effect which has a negative influence on an eddy-current test is a so-called lifting-off effect. The lifting-off effect results from the detector coil lifting off or changing its distance from the test object.

SUMMARY OF THE INVENTION

It is accordingly an object of the invention to provide a scanning head for eddy-current testing, a method for producing a scanning head for an eddy-current test and an eddy-current test method, which overcome the hereinaforementioned disadvantages of the heretofore-known devices and methods of this general type, which make it possible to carry out a quick eddy-current test and in which a lifting-off effect is low.

With the foregoing and other objects in view there is provided, in accordance with the invention, a scanning head for eddy-current testing of a test object having a test surface, comprising a film base having a film surface; a film disposed at the film surface; a probe coil configuration integrated into the film and having an excitation coil and a detector coil; and the film surface matched to the test surface or to a part of the test surface, permitting gap-free movement of the film over the test surface.

Moving the scanning head over the test surface thus results at most in a gap between the film and the test surface caused by manufacturing tolerances or locations of unevenness. The film essentially slides over the test surface.

Matching the film surface to the test surface allows the scanning head to be moved over the test surface virtually without lifting off at all, so that essentially no lifting-off effect occurs. The use of a probe coil configuration in or on a film also allows the scanning head to be constructed with a large probe area. In consequence, the test time can be kept short since a large area is tested whenever the scanning head is passed over the test surface.

The detector coil may be a single coil, but may also be formed from two coils, in particular two coils wound in mutually opposite senses (gradiometer configuration). The detector coil is then essentially sensitive only to magnetic field gradients by using such a gradiometer configuration. In particular, the excitation coil induces at most a small signal in the detector coil.

In accordance with another feature of the invention, the film base is preferably composed of a flexible material, at least adjacent the film surface. In consequence, the film surface can be matched even better to the test surface by pressing the film base against the test surface.

In accordance with a further feature of the invention, the excitation coil and the detector coil preferably have a mutual inductance of less than 1 nH, in particular less than 100 pH. This structure keeps crosstalk from the excitation coil to the detector coil at a low level.

In accordance with an added feature of the invention, the excitation coil preferably also has a conductor cross-section of more than $10^{-3}$ mm$^2$.

In accordance with an additional feature of the invention, the film is preferably at least partially provided with a cooling coating, which is thermally highly conductive and electrically poorly conductive. The film is preferably constructed to be thermally highly conductive and electrically poorly conductive. Furthermore, the film base is preferably constructed to be thermally highly conductive. These measures serve to keep heating low or to carry away the heat that is produced effectively and without damage. These measures make it possible, in particular, to pass a high excitation current through the excitation coil. A high excitation current is desirable in order to increase the measurement sensitivity. A high excitation current results in losses, and thus heating, as a result of the electrical resistance.

In accordance with yet another feature of the invention, the test surface has a roughness with a mean roughness length, and the probe coil configuration preferably has an extent which is considerably greater than the mean roughness length, in a direction lying in the film. In this way, lifting-off effects caused by the roughness are averaged out.

In accordance with yet a further feature of the invention, the detector coil preferably has a greater extent in the film surface in a longitudinal direction than in a transverse direction lying at right angles to the longitudinal direction. This refinement allows increased detector coil sensitivity for elongated material faults, such as cracks which are oriented in the longitudinal direction, when the detector coil is moved transversely with respect to the longitudinal direction.

Furthermore, the detector coil in the film surface can preferably be matched to an imaginary square-function envelope line in such a way that it touches all four sides of the envelope line. As a result of the symmetry of such a structure, the sensitivity of the detector coil is independent of the orientation of elongated material faults.

In accordance with yet an added feature of the invention, the probe coil configuration can preferably be read by a read unit which contains a SQUID sensor. The use of a SQUID sensor increases, in particular, the sensitivity and the signal-to-noise ratio of the measurement apparatus. The probe coil configuration in this case is part of a flux transformer for transmitting the magnetic field to be measured to the highly-sensitive SQUID sensor.

In accordance with yet an additional feature of the invention, the test surface is preferably formed by a wall of a groove in the test object, and the film surface is matched to the wall. As a rule, access to a groove with a conventional scanning head for eddy-current testing is difficult. Even a groove can be tested easily and without any significant interference from the lifting-off effect, by matching the film surface to the groove wall. An eddy-current test can thus be carried out easily and quickly even in the case of complex geometries, such as those formed by a groove.

In accordance with again another feature of the invention, the test surface is preferably a part of a surface of a turbine blade having a root part and a blade section leading edge, in particular a part of a surface of the root part or of a surface of the blade section leading edge. The configuration of the scanning head allows quick and efficient testing of the turbine blades for material faults. The root part and the blade section leading edge of a turbine blade are particularly subject to severe stresses and must be tested regularly. In this case, the adapted scanning head also allows testing to be carried out outside the laboratory, for example directly on the turbine. The capability of carrying out a quick eddy-current test in this case can keep expensive inspection time short. Both gas-turbine and steam-turbine blades as well as the blades of turbine propulsion systems can be tested.

In accordance with again a further feature of the invention, the probe coil configuration is preferably constructed as a photolithographically produced conductor configuration. Particularly in the case of a gradiometric probe coil configuration, that is to say in the case of a detector coil which is formed from two coils wound in opposite senses, the photolithographically produced probe coil configuration allows the two coils of the detector coil to be matched well.

With the objects of the invention in view, there is also provided a method for producing a scanning head for eddy-current testing of a test object having a test surface with a shape, which comprises attaching a moldable material to the test surface without gaps; forming a film base with the material for a probe coil configuration integrated in a film; and matching the film base to the shape of the test surface.

The advantages of such a method correspond to the statements relating to the advantages of the scanning head for an eddy-current test.

In accordance with another mode of the invention, the film is preferably in close contact with the test surface and the material is cast over the film and cured. Such casting of a film which is in close contact with the test surface results in a scanning head that is matched to the test surface being produced in a simple and quick manner.

With the objects of the invention in view, there is additionally provided an eddy-current test method for testing a test object having a test surface, which comprises placing a probe coil configuration integrated into a film at a film surface of a film base on a scanning head; matching the film surface to the test surface for moving the film over the test surface without gaps; and moving the scanning head over the test surface.

The advantages of such an eddy-current test method correspond to the statements relating to the advantages of a scanning head for an eddy-current test.

Other features which are considered as characteristic for the invention are set forth in the appended claims.

Although the invention is illustrated and described herein as embodied in a scanning head for eddy-current testing, a method for producing a scanning head for an eddy-current test and an eddy-current test method, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
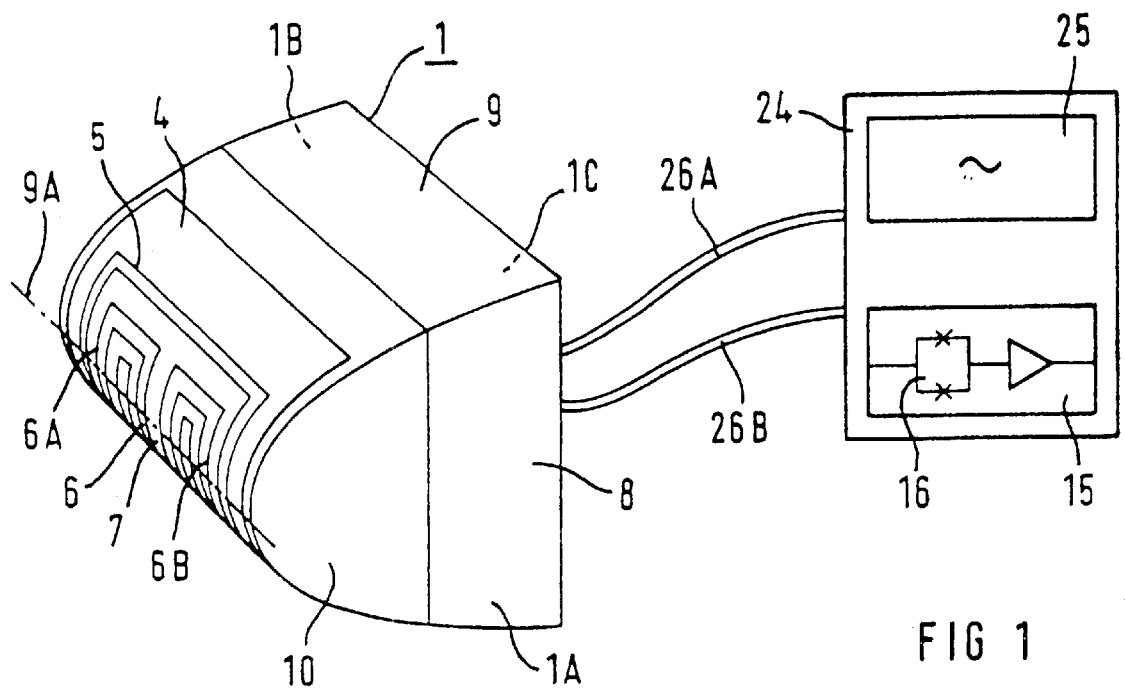
FIG. 1 is a diagrammatic, perspective view of a scanning head with an elevational view of a measurement electronics device.

Referring now in detail to the figures of the drawings, in which the same reference symbols have the same meaning, and first, particularly, to FIG. 1 thereof, there is seen a scanning head 1. The scanning head 1 is connected through leads 26A and 26B to a measurement electronics device 24. The measurement electronics device 24 includes a supply unit 25 which produces an alternating current. The measurement electronics device 24 also includes a read unit 15 in which, in this example, a SQUID sensor 16 is provided. In this example, the scanning head 1 is formed with a roughly U-shaped cross-section. Broad sides of two flat, U-shaped, mutually parallel side surfaces 1A and 1B are connected to narrow sides of a rectangular covering surface 1C, at right angles thereto. A film surface 9 is located between the side surfaces 1A and 1B and is bent along an edge of the side surfaces 1A and 1B. The film surface 9 gives the scanning head a nose-shape. Locations on the film surface 9 that are furthest away from the covering surface 1C form an apex line 9A. A film 4 is disposed on the film surface 9, symmetrically about the apex line 9A. The film 4 is fitted with a probe coil configuration 7. The latter includes an excitation coil 5 which surrounds a detector coil 6. The detector coil 6 is formed by a first coil 6A and second coil 6B. The second coil 6B is wound in the opposite sense to the coil 6A. Approximately half of a film base 8, as measured from the apex line 9A, is composed of a flexible material 10. The excitation coil 5 is connected to the supply unit 25 through the lead 26A. The detector coil 6 is connected to the read unit 15 through the lead 26B.

Figure 2:
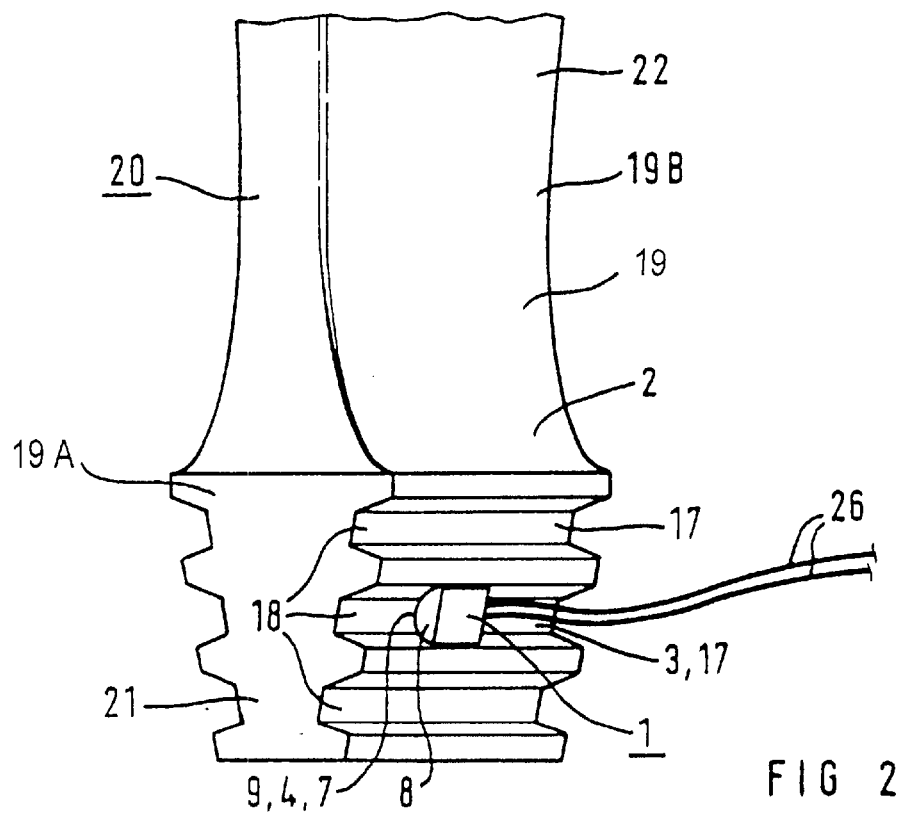
FIG. 2 is a fragmentary, perspective view of a root part of a turbine blade having a scanning head disposed thereon.

FIG. 2 shows a diagrammatic perspective illustration of a turbine blade 20 having a surface 19. The turbine blade 20 has a root part 21 with a surface 19A and a blade section leading edge 22 with a surface 19B. The root part 21 has grooves 18 that run parallel to one another, which gives the root part 21 a characteristic fir-tree profile. Each groove 18 has a groove wall 17. The root part 21 is adjacent the blade section leading edge 22, only a part of which is illustrated. A scanning head 1 is inserted into one of the grooves 18. This scanning head 1 is connected by leads 26 to a supply unit, which is not illustrated, and to a read unit, which is likewise not illustrated. The scanning head 1 has a film base 8. For its part, the film base 8 has a film surface 9. The film surface 9 is matched to a test surface 3, which in this case is a groove wall 17. In consequence, a film 4 which is disposed on the film surface 9 is in contact with the groove wall 17 without any gap. A probe coil configuration 7, as is seen in FIG. 1, is fitted on the film 4.

When the scanning head 1 is used to carry out an eddy-current test method to test a groove 18, the scanning head 1 is drawn through the groove 18. In the process, the excitation coil 5 seen in FIG. 1 is supplied with alternating current through the supply unit 25 seen in FIG. 1. A magnetic field produced by this alternating current induces an eddy current in the groove wall 17. This eddy current in turn results in a magnetic field. This magnetic field is measured by the detector coil 6 seen in FIG. 1. A material fault in the groove 18, for example a crack, then results in an impedance for the eddy current which flows being changed, and thus in the magnetic field being changed. The detector coil 6 is read by the read unit 15 seen in FIG. 1, and changes in the magnetic field measured by the detector coil 6 are displayed as a function of a position of the scanning head 1 in the groove 18. In this way, material faults can be located easily and quickly even if the geometry is complex.

Figure 3:
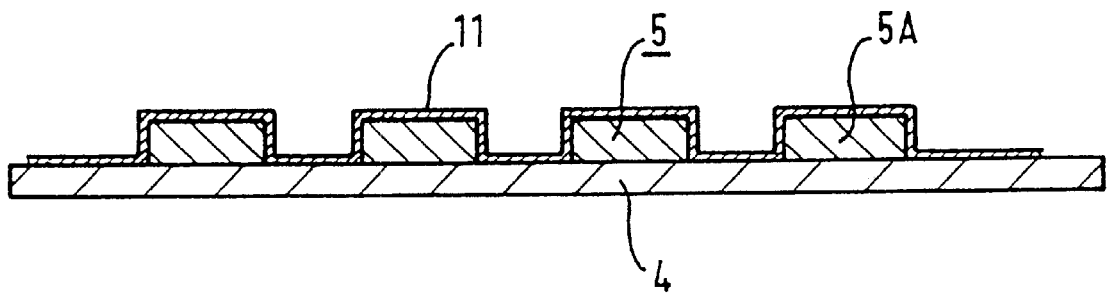
FIG. 3 is a cross-sectional view of a part of an excitation coil.

FIG. 3 shows a cross-section through four turns 5A of an excitation coil 5. The excitation coil 5 is disposed on a film 4. Each turn 5A of the excitation coil 5 has an approximately rectangular cross-section. The film 4 and the turns 5A of the excitation coil 5 are covered with a coating 11 which is thermally highly conductive but electrically poorly conductive. The film 4 may also be composed of thermally highly conductive material. In order to produce a sufficiently high measurement signal, it is desirable that the current which is passed through the excitation coil 5 be as high as possible. This results in losses due to electrical resistance which heats the excitation coil 5 and its environment, in particular the film 4. This can lead to damage to the film 4. In order to keep the electrical resistance low, the cross-sections of the turns 5A are chosen to be greater than $10^{-3}$ mm². The resultant heat is also dissipated through the thermally highly conductive coating 11 and possibly through a thermally highly conductive film 4.

Figure 4:
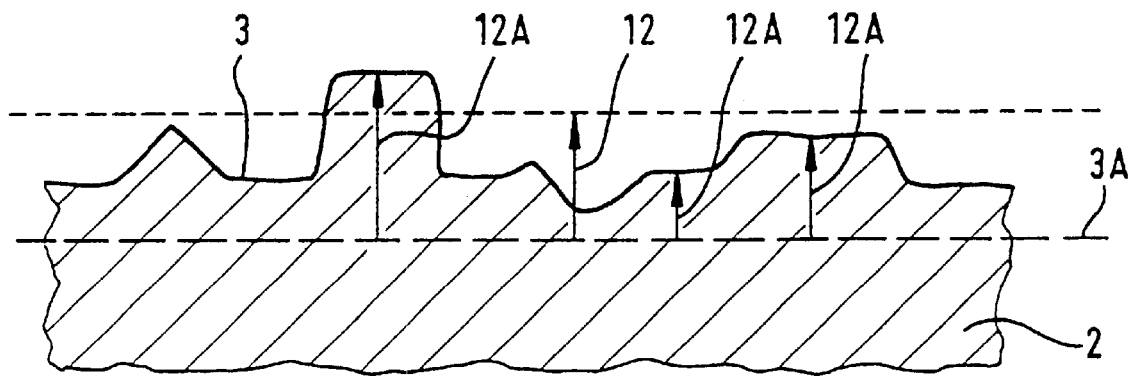
FIG. 4 is an enlarged, fragmentary, cross-sectional view of a test surface.

FIG. 4 shows a cross-section through the test surface 3. The test surface 3 has a roughness which becomes evident in different distances 12A between locations on the test surface 3 and a plane 3A. A mean value of these different distances 12A gives a mean roughness length 12. In order to ensure that the roughness levels of the test surface 3 do not lead to any undesirable lifting-off effect in the case of the eddy-current test method, the probe coil configuration is constructed to be considerably larger, at least in one direction, than the mean roughness length 12. The roughness levels are thus averaged out during a measurement.

Figure 5:
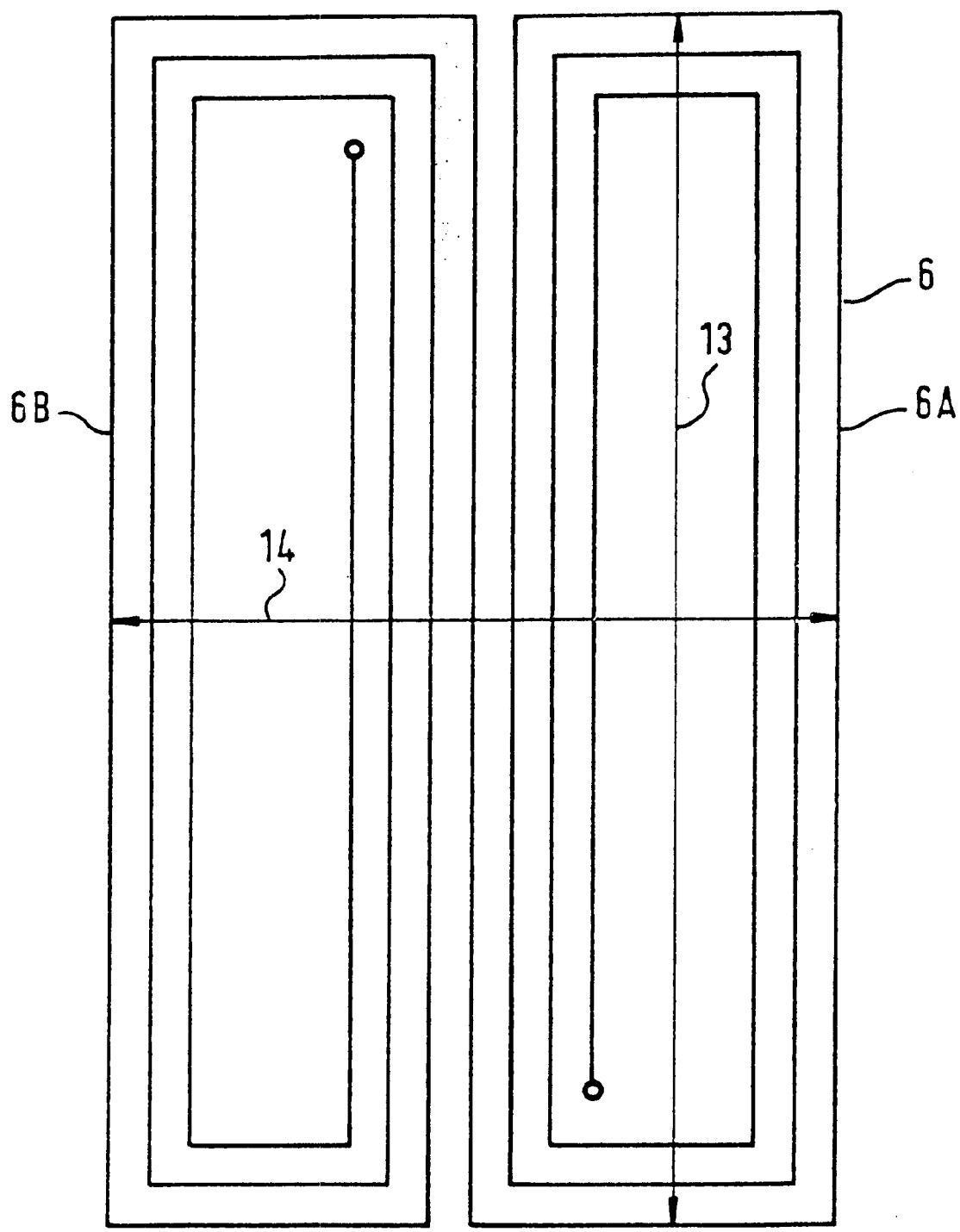
FIGS. 5 to 7 are plan views of embodiments of a detector coil.

FIG. 5 shows a detector coil 6. This detector coil 6 is formed from two coils 6A and 6B which are wound in mutually opposite senses. The detector coil 6 has a greater extent in a longitudinal direction 13 than in a transverse direction 14 lying at right angles to the longitudinal direction 13. In an eddy-current test method, such a detector coil 6 is moved in the transverse direction 14 and has increased sensitivity to material faults which extend transversely with respect to the transverse direction 14.

Figure 6:
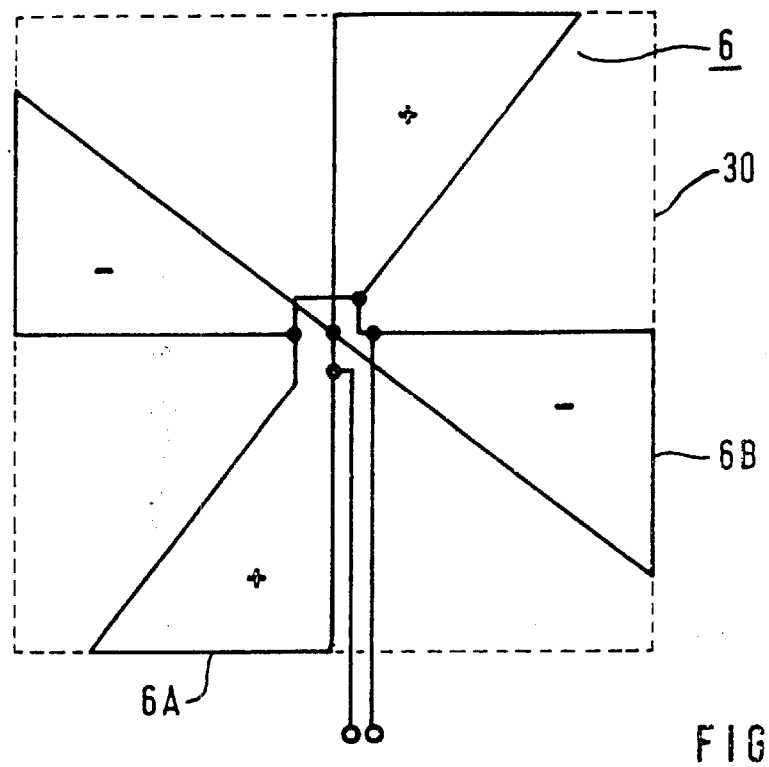
Figure 7:
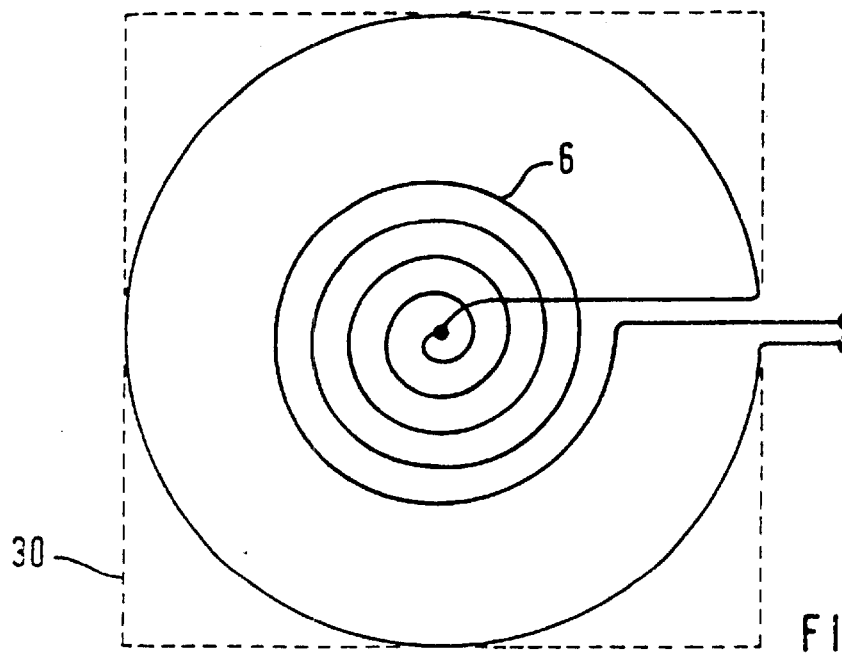

In contrast, FIG. 6 and FIG. 7 show a detector coil 6 which can be respectively matched to a square-function envelope line 30. Both a clover-leaf configuration of the detector coil, as in FIG. 6, and a radially symmetrical detector coil 6, as in FIG. 7, have a sensitivity which does not vary significantly with respect to the measurement direction for elongated material faults that extend in a different direction.

Figure 8:
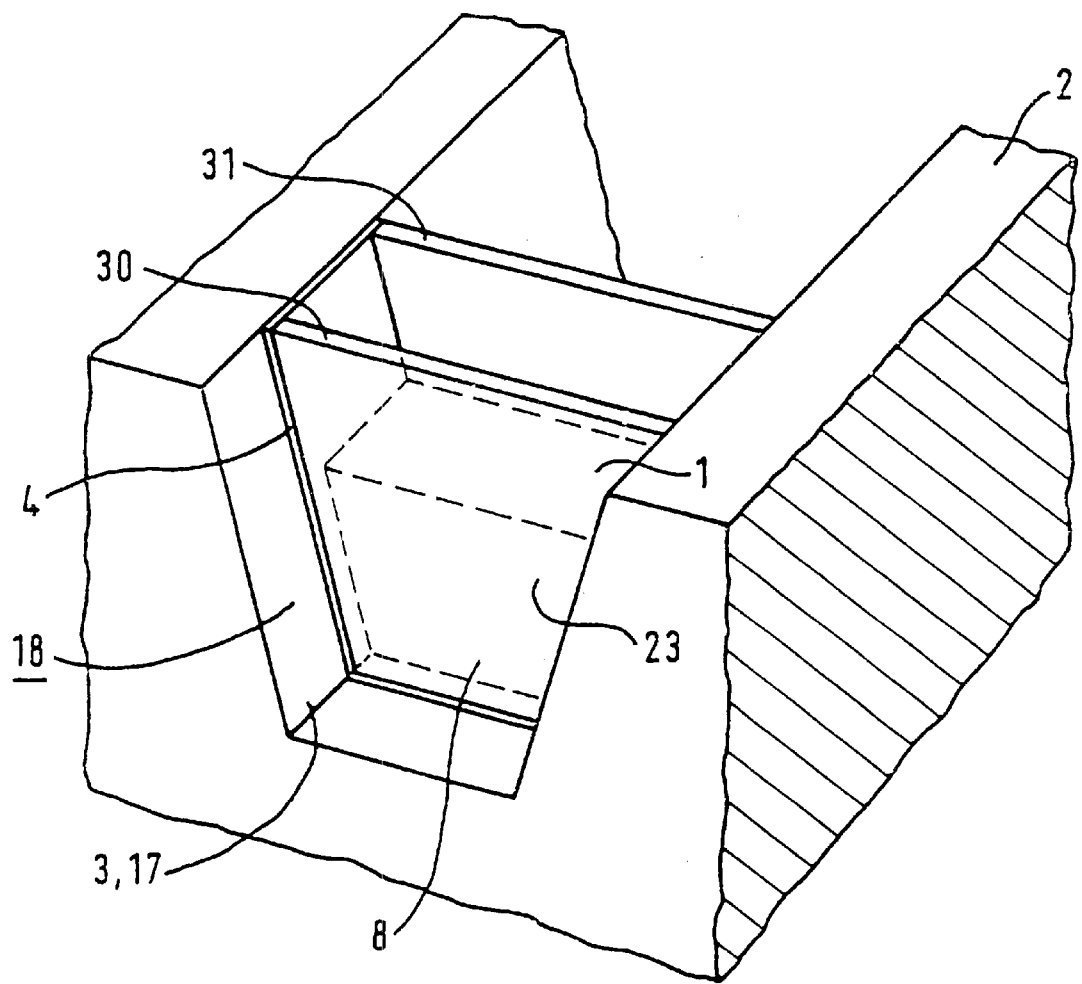
FIG. 8 is a fragmentary, perspective view of a test object illustrating a method for producing a scanning head.

A method for producing a scanning head 1 which is matched to a test surface 3 will be explained with reference to FIG. 8. This figure illustrates a test object 2 having a groove 18 with a roughly trapezoidal cross-section. The groove wall 17 of the groove 18 forms the test surface 3. Two side parts 30 and 31 are each inserted into the groove 18, spaced apart from one another, along a respective cross-section through the groove 18. The two side parts 30, 31 enclose a film 4 having a probe coil configuration which is not illustrated. The film 4 is in close contact with the test surface 3, that is to say with the groove wall 17. A moldable material 23 is cast in a gap between the side parts 30 and 31 up to about half the depth of the groove 18. The mouldable material 23 is curable. Once the moldable material 23 has cured, this produces a scanning head 1 which is accurately matched to the test surface 3, for an eddy-current test.

We claim:

1. In a scanning head for eddy-current testing of a test object having a test surface, the improvement comprising:

a film having a film surface, said film surface matched to at least a part of the test surface, permitting gap-free movement of said film over the test surface;

a film disposed at said film surface; and a probe coil configuration integrated into said film and having an excitiation coil and a detector coil, said detector coil having a clover-leaf configuration with four windings wound in mutually opposite senses, providing a winding direction changing in circumferential direction.

2. The scanning head according to claim 1, wherein said film base is formed of a flexible material, at least adjacent said film surface.

3. The scanning head according to claim 1, wherein said excitation coil and said detector coil have a mutual inductance of less than 1 nH.

4. The scanning head according to claim 1, wherein said excitation coil and said detector coil have a mutual inductance of less than 100 pH.

5. The scanning head according to claim 1, wherein said excitation coil has a conductor cross-section greater than $10^{-3}$ mm².

6. The scanning head according to claim 1, wherein said film is at least partially provided with a cooling coating being thermally highly conductive and electrically poorly conductive.

7. The scanning head according to claim 1, wherein said film is thermally highly conductive and electrically poorly conductive.

8. The scanning head according to claim 1, wherein said film base is thermally highly conductive.

9. The scanning head according to claim 1, wherein the test surface has a roughness with a mean roughness length, and said probe coil configuration has an extent, in a direction lying in said film, being considerably greater than the mean roughness length.

10. The scanning head according to claim 1, including a read unit for reading said detector coil, said read unit containing a SQUID sensor.

11. The scanning head according to claim 1, wherein the test object has a groove formed therein defining a wall forming the test surface, and said film surface is matched to the wall.

12. The scanning head according to claim 1, wherein the test surface is a part of a surface of a turbine blade having a root part and a blade section leading edge.

13. The scanning head according to claim 1, wherein the test surface is a part of a surface of a root part of a turbine blade.

14. The scanning head according to claim 1, wherein the test surface is a part of a surface of a blade section leading edge of a turbine blade.

15. The scanning head according to claim 1, wherein said probe coil configuration is a photolithographically produced conductor configuration.

* * * * *